(12) United States Patent
Buffiere et al.

(10) Patent No.: US 8,580,531 B2
(45) Date of Patent: *Nov. 12, 2013

(54) DETECTION OF ANTIGENS CARRIED BY ERYTHROCYTES AND OF ANTI-ERYTHROCYTE ANTIBODIES

(75) Inventors: Frederic Buffiere, Pessac (FR); Yves Raisin, Ermont (FR); Eliane Rivalin, Aigremont (FR); Amparo Sanjuan, Issy-les-Moulineaux (FR)

(73) Assignee: Bio-Rad Innovations, Marnes La Coquette (FR)

( * ) Notice: Subject to any disclaimer, the term of this patent is extended or adjusted under 35 U.S.C. 154(b) by 421 days.

This patent is subject to a terminal disclaimer.

(21) Appl. No.: 12/601,827

(22) PCT Filed: Jun. 6, 2008

(86) PCT No.: PCT/EP2008/057128
§ 371 (c)(1),
(2), (4) Date: Nov. 25, 2009

(87) PCT Pub. No.: WO2008/148890
PCT Pub. Date: Dec. 11, 2008

(65) Prior Publication Data
US 2010/0184101 A1    Jul. 22, 2010

Related U.S. Application Data

(60) Provisional application No. 60/929,052, filed on Jun. 11, 2007.

(30) Foreign Application Priority Data

Jun. 8, 2007 (FR) .................................. 07 55624

(51) Int. Cl.
*G01N 33/00* (2006.01)
*G01N 33/554* (2006.01)

(52) U.S. Cl.
USPC ........ 435/7.25; 435/7.1; 435/287.2; 436/513; 436/518; 436/519; 436/520; 436/521; 436/522; 436/523; 436/526; 436/533; 436/534; 436/10; 436/63; 436/172; 436/175; 422/73; 422/82.08; 422/82.09

(58) Field of Classification Search
USPC ............ 435/5, 7.1, 7.2, 7.25, 287.2; 436/513, 436/518–523, 526, 533, 534, 10, 56, 63, 436/171, 172, 175; 422/68.1, 73, 82.08, 422/82.09
See application file for complete search history.

(56) References Cited

U.S. PATENT DOCUMENTS 4,810,632 A    3/1989  McMillan
5,776,711 A *  7/1998  Vyas et al. ................... 435/7.25

(Continued)

FOREIGN PATENT DOCUMENTS

WO    WO 85/01354    3/1985
WO    WO 98/21593    5/1998

OTHER PUBLICATIONS

Everett et al. Class I HLA molecules on human erythrocytes, Quantitation and transfusion effects. Transplantation 44 (1): 123-129 (Jul. 1987).*
Garratty, G. et al. "Applications of flow cytofluorometry to transfusion science" *Transfusion*, Jan. 1995, pp. 157-178, vol. 35, No. 2, XP-000983723.
Freedman, J. et al. "Applications of Flow Cytometry in Transfusion Medicine" *Transfusion Medicine Reviews*, Apr. 1995, pp. 87-109, vol. 9, No. 2, XP-005441355.
Wood, B. L. et al. "Increased erythrocyte phosphatidylserine exposure in sickle cell disease: flow-cytometic measurement and clinical associations" *Blood*, Sep. 1, 1996. pp. 1873-1880, vol. 88, No. 5, XP-002491960.
Written Opinion in International Application No. PCT/EP2008/057128, Aug. 12, 2008, pp. 1-10.

*Primary Examiner* — Gail R Gabel
(74) *Attorney, Agent, or Firm* — Saliwanchik, Lloyd & Eisenschenk

(57) ABSTRACT

The invention relates to a method for detecting a plurality of antigenic molecules carried by erythrocytes and/or a plurality of anti-erythrocyte antibodies, said antigenic molecules carried by the erythrocytes consisting of antigenic molecules carried not only by the erythrocytes, but also by at least one other cell population, other than the blood group antigen molecules, said method comprising bringing a sample into contact with distinguishable beads, on which are attached a) antibodies specific for said antigens, or b) erythrocytes or erythrocyte membrane fragment.

27 Claims, 9 Drawing Sheets

(56) References Cited

U.S. PATENT DOCUMENTS

| | | | |
|---|---|---|---|
| 5,948,627 A | 9/1999 | Lee et al. | |
| 6,913,935 B1 * | 7/2005 | Thomas | 436/518 |
| 7,332,349 B2 * | 2/2008 | Yang et al. | 435/7.24 |
| 2001/0054580 A1 | 12/2001 | Watkins et al. | |
| 2010/0178656 A1 * | 7/2010 | Buffiere et al. | 435/7.1 |

* cited by examiner

DETECTION OF ANTIGENS CARRIED BY ERYTHROCYTES AND OF ANTI-ERYTHROCYTE ANTIBODIES

CROSS-REFERENCE TO RELATED APPLICATION

This application is the U.S. national stage application of International Patent Application No. PCT/EP2008/057128, filed Jun. 6, 2008, which claims the benefit of U.S. Provisional Patent Application No. 60/929,052, filed Jun. 11, 2007, the disclosures of which are hereby incorporated by reference in their entirety, including all figures, tables and amino acid or nucleic acid sequences.

The invention takes advantage of the presence of antigenic molecules on erythrocytes for identifying the antigenic molecules which are carried both by erythrocytes and by other cell populations.

Blood transfusion nowadays consists in intravenously administering preparations of red blood cell concentrates (blood cell concentrates) obtained from blood donors. When there is a blood transfusion, the primary risk is linked to the possibility of an antibody and its erythrocyte antigen being reunited in the body of the recipient (the individual transfused). There are in fact, at the surface of erythrocytes, also called red blood cells, membrane antigens, in particular blood group (or system) antigens, capable of being recognized by the immune system and of triggering an immune response with red blood cell haemolysis. The consequences of such an immunological reaction may range from inefficient transfusion with no clinical sign, to a slight clinical reaction (anxiety, shivers), serious clinical reaction (shock, haemoglobinurea, renal insufficiency) or dramatic clinical reaction (shock, disseminated intravascular haemolysis) resulting in death.

The donor's red blood cells are said to be compatible with the recipient's blood if the recipient does not have any circulating antibodies directed against an erythrocyte antigen of the donor.

In addition to blood group antigens, the presence of HLA antigenic determinants on erythrocytes has been detected in 15% of individuals in the French population (de Villartay et al., Tissue Antigens, 1985, 26(1):12-9). Although this amount of HLA antigenic determinants on erythrocytes is low compared with other cell types, it is nevertheless significant in terms of transfusion risk (Everett et al., Transplantation, 1987, vol. 44, no. 1, pp. 123-129).

The inventors, focusing initially on transfusion risk, have then realized that, in addition to blood group antigen molecules, any antigenic molecule could be readily detected by taking advantage of their incidental presence on erythrocytes.

SUMMARY OF THE INVENTION

The invention provides an in vitro method for identifying a plurality of antigenic molecules carried by the erythrocytes of an individual, and/or for identifying a plurality of antibodies against antigenic molecules carried by erythrocytes, in a biological sample, said antigenic molecules carried by the erythrocytes consisting of antigenic molecules carried both by the erythrocytes and by at least one other cell population, other than the blood group molecules, said method comprising
a) identifying a plurality of antigenic molecules carried by the erythrocytes of an individual, by
  (i) bringing said sample containing erythrocytes into contact, in a single test receptacle, or in several separate test receptacles, with groups of distinguishable beads, each group of distinguishable beads carrying a given antibody, specific for an antigenic molecule carried by erythrocytes, which differs from one group of beads to the other, under conditions which allow the erythrocytes to bind to the antibodies, without agglutination, said erythrocytes being labelled before or after they have been brought into contact with said groups of beads,
  (ii) eliminating the erythrocytes which have not bound to said antibodies, and
  (iii) identifying the group of beads having bound the labelled erythrocytes, thereby allowing the identification of the antigens carried by the erythrocytes detected; and/or
b) identifying a plurality of antibodies against antigenic molecules carried by erythrocytes, in a biological sample, by
  (iv) bringing said sample into contact, in a single test receptacle, or in several separate test receptacles, with groups of distinguishable beads, each group of distinguishable beads carrying (1) erythrocytes or (2) erythrocyte membrane fragments, of known phenotype which differs from one group of beads to the other, under conditions which allow the antibodies or the activated serum complement fractions present in the sample to bind to the erythrocytes or to the erythrocyte membrane fragments, without agglutination,
  (v) eliminating the antibodies or activated serum complement fractions which have not bound to said erythrocytes or to said erythrocyte membrane fragments,
  (vi) labelling the bound antibodies and/or the bound activated serum complement fractions, and
  (vii) identifying the group of beads having bound the labelled antibodies or the labelled activated serum complement fractions, thereby allowing the identification of the antibodies against antigenic molecules carried by the erythrocytes, that are present.

The invention also provides a set of reagents for implementing this method, comprising groups of distinguishable beads, each carrying at least one particular physical parameter that can be detected, and belonging to at least two different groups, one of the groups carrying a capture antibody specific for an antigenic molecule carried by erythrocytes, and the other group carrying (1) erythrocytes or (2) an erythrocyte membrane fragment.

DETAILED DESCRIPTION OF THE INVENTION

Definitions

In the present description, the terms "erythrocyte", or "red blood cell" are used indifferently to denote the same blood cell.

The term "multiplex" means that several different antigen-antibody-type reactions are analyzed simultaneously for a single sample in a single receptacle and using a single signal-reading system.

The term "simplex" means that the antigen-antibody-type reactions are analyzed in several separate receptacles. Preferably, the analyses are nevertheless carried out simultaneously, and preferably using a single signal-reading system.

The expression "antigenic molecule carried by erythrocytes" denotes any antigenic molecule carried by erythrocytes, consisting of antigenic molecules which are carried both by erythrocytes and by at least one other cell population. The blood group molecules are excluded here. The term "blood group antigen" is intended to mean any antigen of the ABO system with the A antigen, the B antigen, the A and B antigens expressed simultaneously or the H antigen, of the Rhesus system with the D, E, e, and C or c antigens, of the Kell system with the K or k antigen, of the Duffy system (Fya, Fyb), of the Kidd system (Jka, Jkb) system or else of other systems that are less commonly investigated in practice but that also exist, such as MNS, Lewis, etc.

The cell populations carrying the antigenic molecules of interest may be blood cells (lymphocytes), platelets being included.

Examples of antigenic molecules of interest carried by erythrocytes and other cell populations include the molecules of the HLA system, in particular HLA B-27, CD55 and/or CD29 (Terpos et al., Medical Science Monit. 2008, 14 276-280). Other examples of antigenic molecules of interest include erythrocyte ageing markers, for example phosphatidylserine (PS).

Erythrocyte antigens which are found physiologically or not at the surface of erythrocytes, and at the surface of other cell types or populations, are included. Antigens present at the surface of erythrocytes resulting from immunological reactions due to erythrocyte antigens are also included. In this case, the expression "antigenic molecule carried by erythrocytes" comprises antibodies or elements of the serum complement fraction, carried by erythrocytes sensitized in vivo. The antigenic molecules not found physiologically include, for example, chemical products or medicaments, absorbed by the individual, or degradation products thereof.

Also included are antigenic molecules adsorbed onto the erythrocytes but originating from other cell populations.

The term "carried by erythrocytes" refers to a membrane expression, an adsorption, or an intercellular expression, the antigenic molecules becoming accessible by treatment, or by virtue of a physiological process of the erythrocyte (for example during senescence of the erythrocyte).

The expression "antibody against antigenic molecules carried by erythrocytes" or "anti-erythrocyte antibody" denotes any antibody which binds specifically to antigen carried by erythrocytes, and by at least one other cell population. The term "labelling of the bound antibodies and/or of the bound serum complement fractions" is understood to mean labelling of the antibodies or (optionally activated) serum complement fractions which are reversibly bound or directly embedded in the erythrocyte membrane.

The term "individual" is intended to mean any animal having a plurality of antigenic molecules carried by erythrocytes. As animals, mention may, for example, be made of the dog, in which eight different blood groups have been identified to date, and the cat, which has three. Of course, the term "individual" also relates to human beings, including at the foetal stage.

The term "biological sample" is intended to mean any fraction of a body fluid or of a tissue biopsy that may contain erythrocytes or anti-erythrocyte antibodies, whether physiologically or pathologically. As a biological sample, mention may therefore be made of a blood sample, and in particular a whole blood sample or a blood cell pellet sample (or a blood bag), or any other blood preparation, but also saliva, sweat, tears, milk or urine when it contains blood. It is also possible to use a plasma or serum sample for antibody screening. The sample used in mode (a) for detecting antigenic molecules may be identical to or different from the sample used for detecting antibodies. When the sample is identical, modes (a) and (b) can be carried out in the same receptacle, simultaneously. The biological sample may have undergone no pre-treatment.

The term "antibody" refers to any whole antibody or functional fragment of an antibody comprising or consisting of at least one antigen combination site, which allows said antibody to bind to at least one antigenic determinant of an antigenic compound.

By way of example of antibody fragments, mention may be made of Fab, Fab' and F(ab')2 fragments and also scFv chains (single chain variable fragment), dsFv chains (double-stranded variable fragment), etc. These functional fragments may in particular be obtained by genetic engineering.

The term "capture antibody" is intended to mean an antibody or a part of an antibody attached to a solid phase, which is capable of retaining at least one antigenic determinant of an antigenic compound present in a biological sample, by affinity binding.

The antibodies used as detection tools may be polyclonal or monoclonal antibodies. The production of monoclonal antibodies or of polyclonal antibodies that can be used in the context of the invention comes under conventional techniques.

The monoclonal antibodies may be obtained according to the conventional lymphocyte fusion and hybridoma culture method described by Köhler and Milstein (Nature, 256, p. 495-497 (1975)). Other methods for preparing monoclonal antibodies are also known (Harlow et al. editors, Antibodies A Laboratory Manual, Cold Spring Harbor Laboratory (1988)). The monoclonal antibodies may be prepared by immunizing a mammal (for example, a mouse, a rat, a rabbit or even a human being, etc.) and by using the technique of lymphocyte fusion producing hybridomas (Köhler and Milstein, 1975, above).

Alternative techniques to this customary technique exist. Monoclonal antibodies can, for example, be produced by expression of a nucleic acid cloned from a hybridoma. Antibodies can also be produced by the phage display technique, by introducing antibody cDNAs into vectors, which are typically filamentous phages (for example, fUSE5 for *E. coli*, Scott et al. (Science, 249, pp. 386-390 (1990)). The latter constitute libraries and have scFv fragments at their surface. Protocols for constructing these antibody libraries are described in Marks et al. (J. Mol. Biol., 222, pp. 581-597, (1991)).

The polyclonal antibodies can be obtained from the serum of an animal immunized against an antigen, preferably of peptide nature, according to the usual procedures.

In general, a polypeptide, in particular a recombined polypeptide, or an oligopeptide can be used, for example, as immunogen. According to a conventional protocol, rabbits are immunized with the equivalent of 1 mg of the peptide immunogen, according to the procedure described by Benoit et al. [PNAS USA, 79, pp. 917-921 (1982)].

Beads:

The beads generally consist of polymers that are inert with respect to the constituents of the biological samples; they are solid and insoluble in the samples. The polymers used may be polyesters, polyethers, polyolefins, polyamides, polysaccharides, polyurethanes or celluloses. Binders may also be used to give the particles integrity and structure. Functional groups may be incorporated with these polymers so as to allow the attachment or the coupling of macromolecules of biological interest (proteins, lipids, carbohydrates, nucleic acids). These functional groups, which are known to those skilled in the art, may be amine ($-NH_2$) or ammonium ($-NH_3^+$ or $-NR_3^+$) functions, alcoholic functions ($-OH$), carboxylic functions ($-COOH$) or isocyanate functions ($-NCO$). The monomers most commonly used for introducing COOH functions into polyolefins are acrylic acid or methacrylic acid.

The attachment of reagents to the surface of the beads can be carried out by electrostatic attractions, affinity interactions, hydrophobic interactions or covalent coupling. Covalent coupling is preferred.

The beads used in the invention are particles approximately spherical in shape, of sizes that may be between 0.5 and 40 µm, preferably between 4 and 9, and more particularly between 5 and 8 µm.

The beads used here are "distinguishable" in that they have differential markers which make it possible to distinguish them from one another by means of an appropriate detector. Each group of beads therefore has different physicochemical properties (size, density, particle size, roughness, absorbence, fluorescence, paramagnetic components) which make it possible to differentiate them from one another by means of suitable detectors or tools, for example a flow cytometer.

As a differential parameter for distinguishing the particles from one another, use may in particular be made of the size of the particles, by choosing non-overlapping size ranges. In another preferred embodiment, the distinguishable particles emit fluorescence signals. The beads which incorporate various fluorescent labels can in fact be distinguished by their fluorescence spectrum. For this, the beads can be impregnated with one or more dyes (for example, fluorescent, luminescent, etc.), where appropriate at various concentrations, or with a label of radioisotope type, enzyme type, etc. (Venkatasubbarao S. <<Microarrays-Status and prospects>> Trends in Biotechnology December 2004, 22(12):630-637; Morgan et al, <<Cytometric bead array: a multiplexed assay platform with applications in various areas of biology>>, Clin. Immunol. (2004) 100:252-266). Scattering or emission of light, or a combination thereof, can also be used to distinguish between the particles.

In a preferred embodiment, the distinguishable beads emit luminescent or fluorescent signals.

The beads used may be superparamagnetic, magnetic or magnetizable. As beads that can be used according to the invention, mention may in particular be made of those described in U.S. Pat. No. 6,872,578. According to a particularly preferred embodiment, the beads used are fluorescent and superparamagnetic. These physicochemical properties may make it possible, during the reaction with the biological sample, to separate the fractions captured by these microparticles from those which are not bound. This separation can be carried out, inter alia, by centrifugation, filtration or magnetization. Separation by magnetization is preferred, and for this, beads containing paramagnetic, ferromagnetic, ferrimagnetic and metamagnetic components may be used. Paramagnetic components are preferred, for instance iron, cobalt, nickel or metal oxides such as $Mn_2O_3$, $Cr_2O$ or $Fe_3O_4$. The amount of magnetic components may be between (by weight) 2% and 50%, and preferably between 3% and 25%.

The antibodies may be attached to the beads by any appropriate technique. They may be attached by direct covalence, or noncovalently, in particular by passive adsorption or by affinity. The direct covalent attachment may be carried out by means of activation of the carboxylic groups present at the surface of the beads, involving bonding via hydroxysuccinimide or carbodiimide, for example. In a specific embodiment, anti-immunoglobulin antibodies are first attached to the beads, by covalence, and then the beads are brought into contact with the antibodies to be attached.

The erythrocytes or the erythrocyte membrane fragments can be attached to the beads by noncovalent bonding via a poly-L-lysine, or by means of any type of ligand such as polycations of dye type. The erythrocytes or the erythrocyte membrane fragments can also be attached to the beads by covalent bonding, in particular using sodium periodate. It has been noted, surprisingly, that the attachment of the red blood cells or of the membrane fragments, whether covalent or noncovalent, does not impair the property that the beads have of being distinguishable according to a flow cytometry process.

The beads are subjected to measurement by a detector such as a flow cytometer, as described, for example, in Luminex patent application WO 97/14028. Thus, subgroups of beads carrying a reactant (antibody or erythrocyte or erythrocyte membrane) are exposed to a biological sample, each subgroup having one or more classification parameters which make it possible to distinguish the beads of one subgroup from those of another subgroup. The beads thus exposed to the sample then go through an examination zone (for example a flow cytometer), where the data relating to the classification parameters (for example, the fluorescence emission intensities) are collected, and preferably also the data relating to the presence or absence of a complex formed between the reactant and the analyte of interest (namely between the bead and the antigenic molecule carried by the erythrocyte according to (a) or the antibody according to (b) in the method of the invention).

Labelling:

The detectably labelled erythrocytes can be labelled by any technique known to those skilled in the art. They may, for example, be labelled with a fluorescent compound, for example a fluorophore which is inserted into the membrane of these cells. They may also be labelled using a ligand which is itself functionalized with a fluorescent label, this ligand being capable of recognizing structures at the surface of the erythrocytes. These ligands may, for example, be antibodies or animal or plant lectins. These types of labelling may or may not be carried out prior to the test.

In the case of antibody identification, it is the antibodies which are labelled, or alternatively it is the (optionally activated) serum complement fractions. Any labelling technique is possible. The types of labelling can also be mixed.

According to a specific embodiment, the antibodies are brought into contact with an anti-human immunoglobulin antibody carrying a fluorescent, luminescent or radioactive label.

According to another specific, optionally cumulative, embodiment, the activated serum fractions are brought into contact with an antibody which specifically recognizes the activated serum complement fractions, said antibody carrying, for example, a fluorescent, luminescent or radioactive label. Such antibodies may be monoclonal or polyclonal and are well known to those skilled in the art.

Elimination of the Unbound Reagents:

Before carrying out the analysis step, the reagents which have not bound during the bringing into contact and the incubation of the reagents should be eliminated. It is desirable to eliminate as much unbound reagent as possible in order to reduce the background noise and therefore to obtain good specificity of the test, but conditions that are too drastic could reduce the sensitivity of said test. A residual presence of unbound reagents is therefore generally tolerable. The conditions for obtaining an acceptable compromise between the sensitivity and the specificity of the method can be readily determined by those skilled in the art by means of routine experiments.

The elimination of the unbound reagents can be carried out by any technique known to those skilled in the art, such as washing by means of repeated centrifugation steps or the use of the superparamagnetic nature of the beads and use of a magnet.

Preferred Embodiments

As defined above, the method according to the invention makes it possible to identify the antigens, or also to identify the antibodies or the serum complement fractions that are bound. It also makes it possible to use combinations of several types of identification. Thus, the identification of the antigens and the identification of the antibodies can be carried out simultaneously or separately. The identification of the antibodies can be carried out by revealing both the antibodies and the serum complement fractions.

The receptacle may be any solid container, for example a test tube, a microplate well or any receptacle that allows reactions in an automated system. It is not necessary to centrifuge the receptacles.

The mixing of the reactants and of the analyte of interest is carried out under conditions (in particular of pH, temperature, ionic strength, etc.) which allow specific binding of the antigens carried by the erythrocytes, to the antibodies, without agglutination. The substantial absence of agglutination makes it possible to use in particular a flow cytometer. In order to avoid any agglutination reaction, it is advantageous to adjust the amount and the size of the beads, and also the concentration of the sample. The agglutination reactions satisfy mathematical laws which have in particular been described by H. E. Hart, Bulletin of mathematical biology, vol 42, 17-36, by K. C. Chak, Bulletin of mathematical biology, vol 42, 37-56 and by C. DeLisi, Journal of Theoretical Biology, 1974, vol 45, pages 555-575. These laws involve several parameters such as, in particular, the size of the reagents and also their ratio by number. Those skilled in the art will therefore choose the reaction conditions by applying these mathematical laws as a function of the reagents that they use, such that no substantial agglutination occurs. For example, when erythrocytes and beads of size similar to those of the erythrocytes, i.e. of the order of 7 μm, are used, those skilled in the art will choose a ratio of the number of erythrocytes to the number of beads ranging from 30 to 150.

Advantageously, it is preferable to provide for a step of chemical or enzymatic degradation of the haemoglobin, such as a haemolysis, preferably after the attachment and before the identification of the antigens or of the antibodies.

The haemolysis can be carried out in various ways. For example, the mixture can be incubated in a medium of low osmolarity. The term "medium of low osmolarity" is intended to mean in general a medium having an osmolarity of less than or equal to 100 mosmol/L. As suitable medium of low osmolarity, mention may be made of ammonium chloride solutions having a concentration of 40 mM or less, or distilled water. The haemolysis may also be carried out by sonication.

Applications:

The method makes it possible to carry out an identification of antigenic molecules carried by erythrocytes, in a multiplex format.

In addition, the method makes it possible, for example through analyzing fluorescence signals, to quantitatively determine the proportion of antigens at the surface of the erythrocytes in the sample.

The method of the invention also makes a quantification of the antibodies possible. Thus, the result obtained may be in numerical form, and available for facilitated interpretation by means of an electronic data processing system.

Advantageously, the method makes it possible to obtain complete, reliable results in only a few minutes. More specifically, it is possible to give a complete result in less than one hour, or even in less than 30 minutes.

The method of the invention also makes it possible to considerably reduce the volume of the test sample taken. Today reactions are generally carried out with a test sample of 25 μl for each test. To carry out the method of the invention, 50 to 100 μl only are, for example, sufficient.

The following figures and examples illustrate the invention without limiting the scope thereof.

FIGURE LEGEND

Figure 5A:
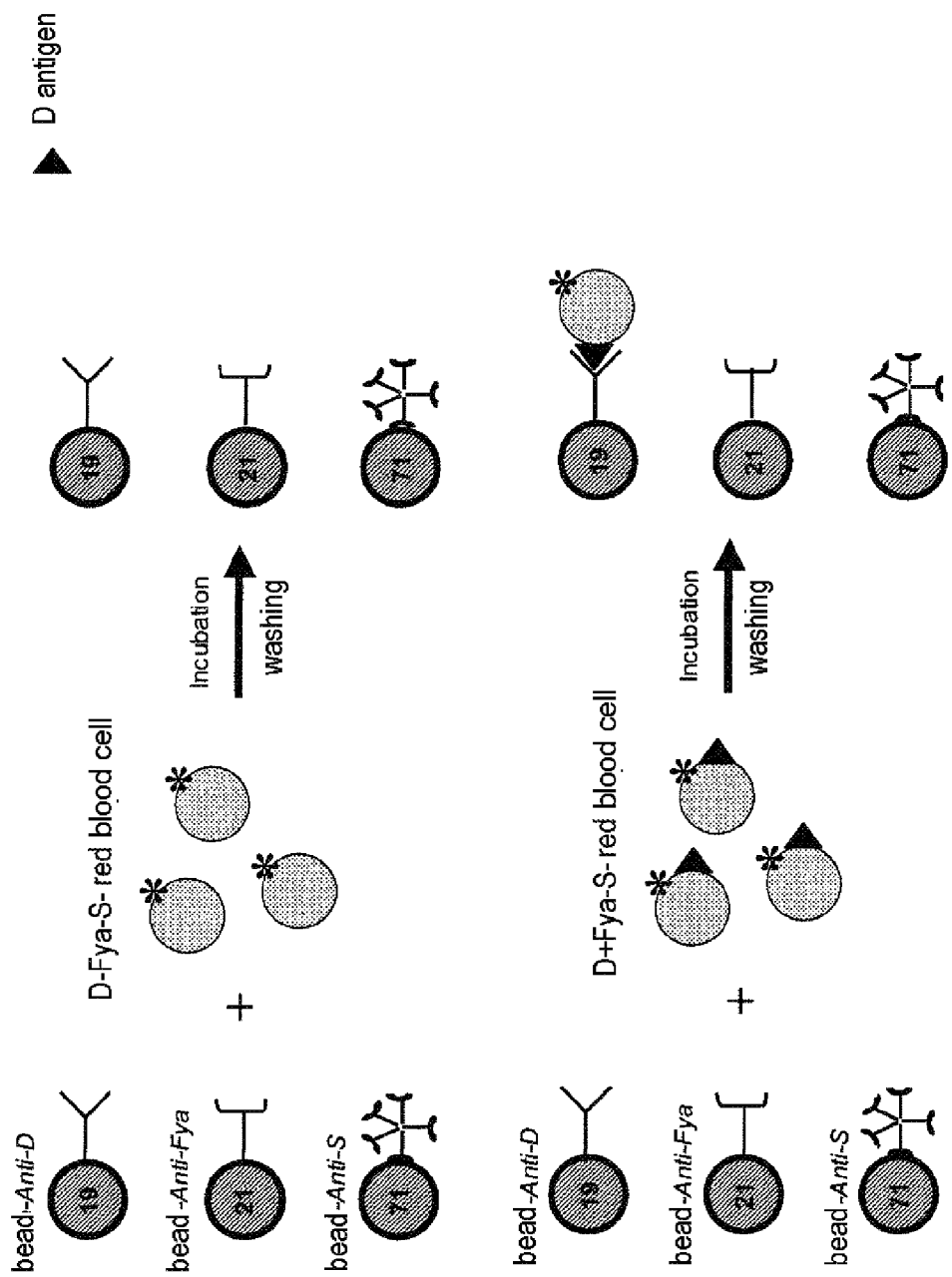
Figure 5B:
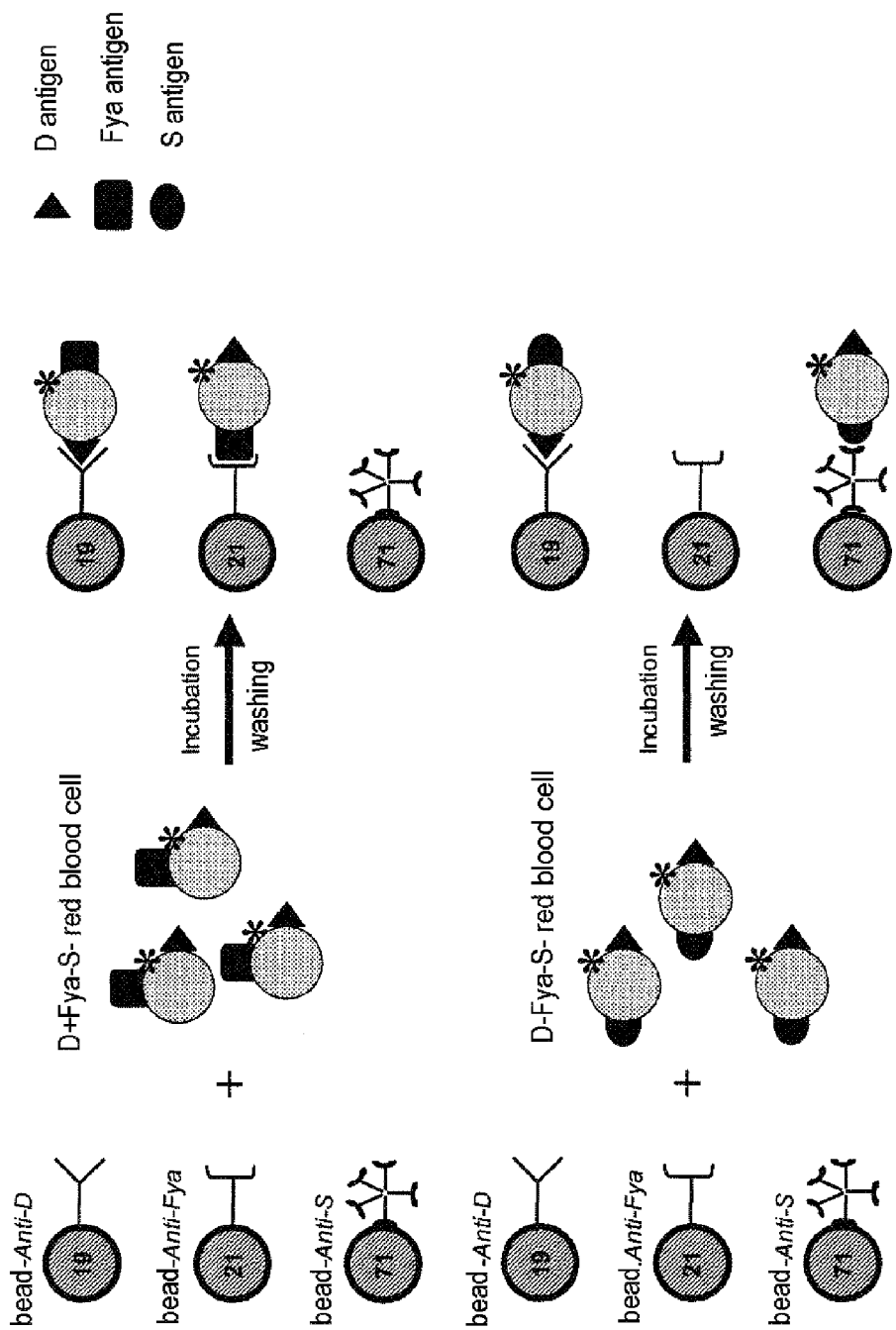
Figure 5C:
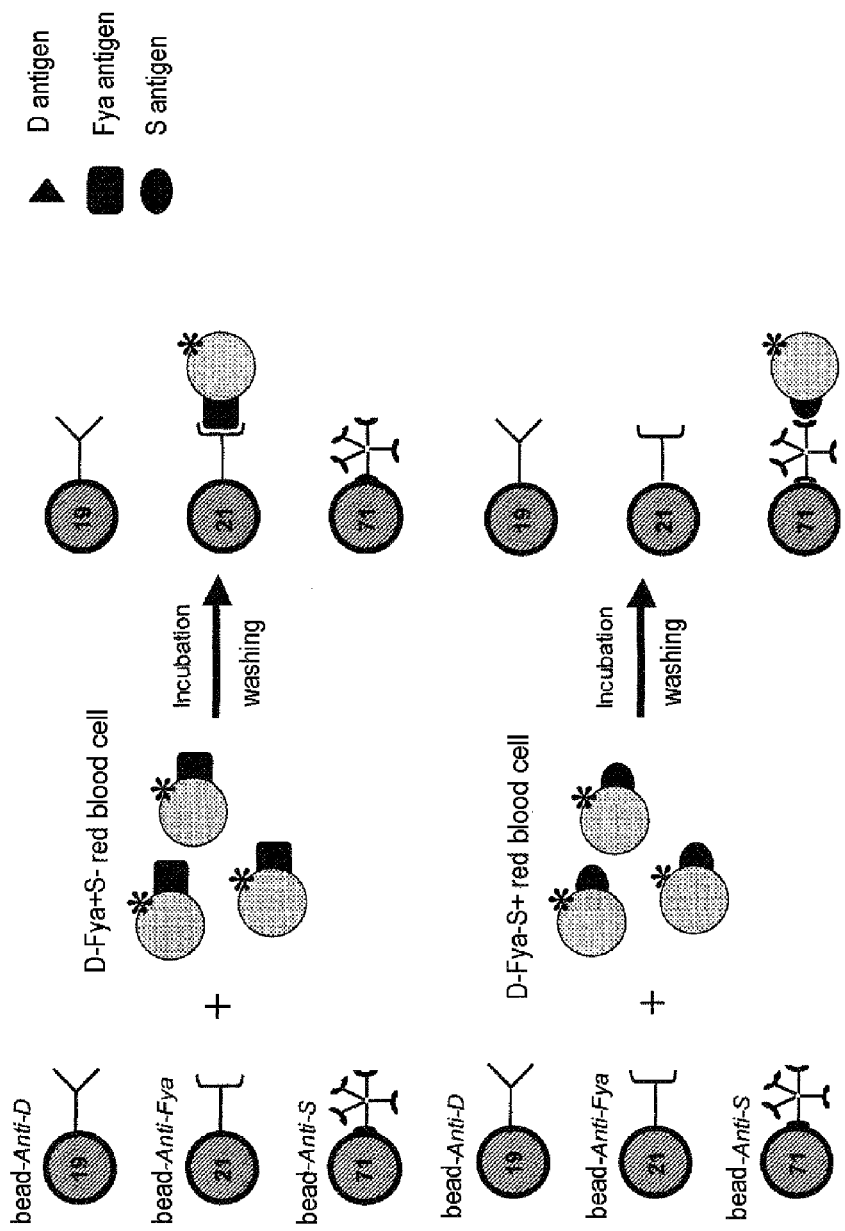
Figure 5D:
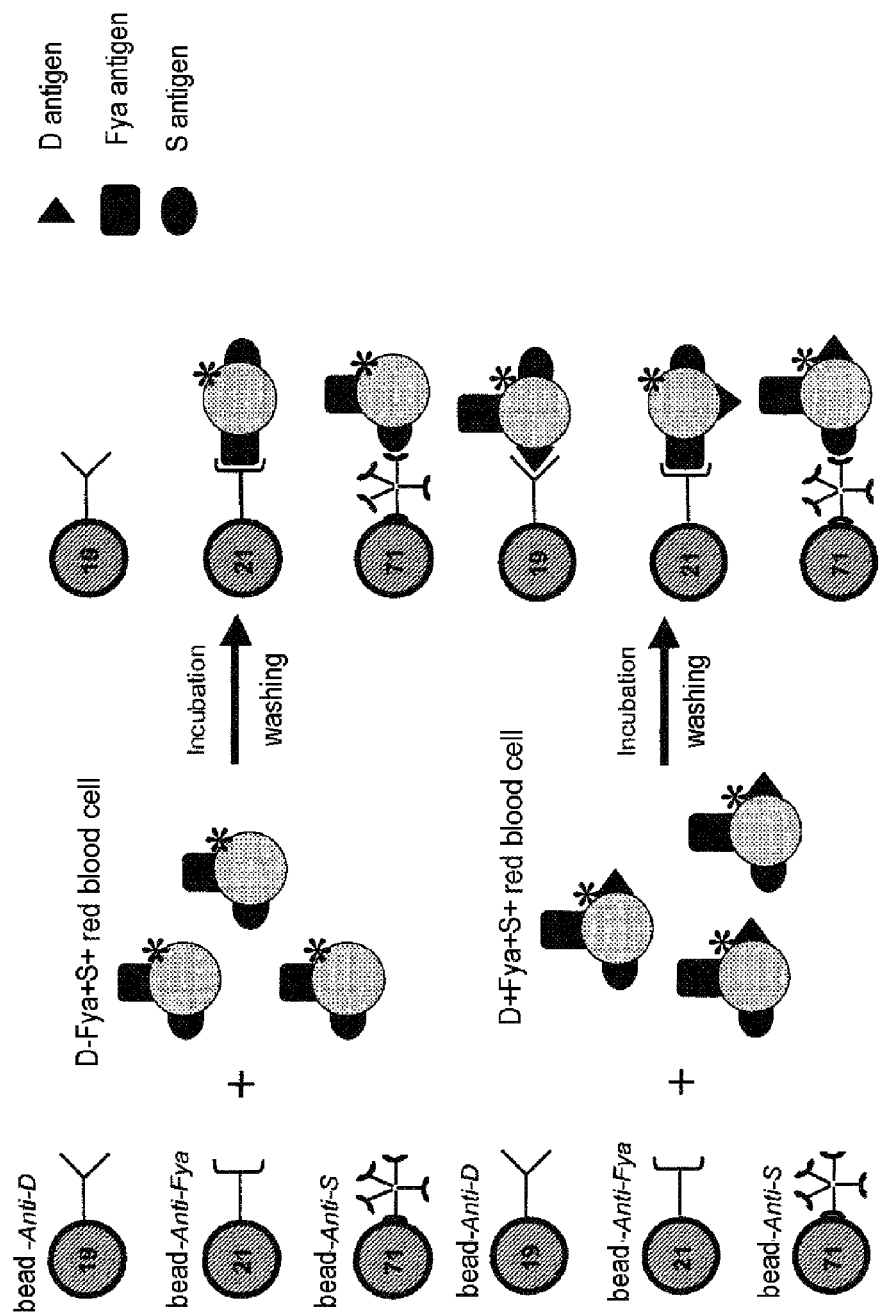

FIGS. 5A to 5D show various embodiments of multiplexed phenotyping of red blood cells. FIGS. 5A and 5C illustrate phenotyping in which erythrocytes are negative for a cell surface antigen or have a single antigen that is bound by a bead carrying an antibody specific for a given antigenic molecule. FIG. 5B depicts phenotyping in which erythrocytes have a pair of antigens that are bound by a bead carrying an antibody specific for a given antigenic molecule. FIG. 5D depicts phenotyping in which erythrocytes have two or three antigens that are bound by a bead carrying an antibody specific for a given antigenic molecule.

Figure 6:
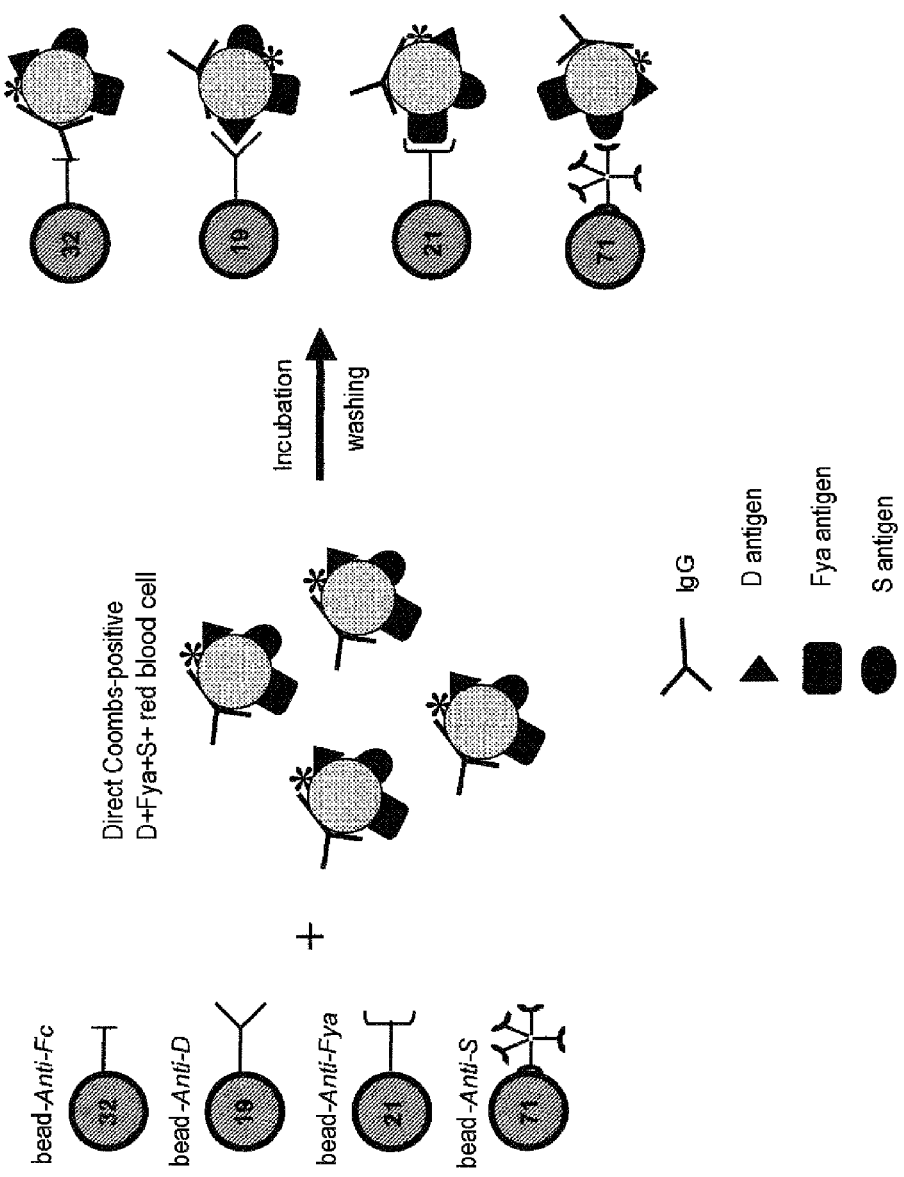

FIG. 6 is a scheme which illustrates the simultaneous identification and multiplexed phenotyping of red blood cells from a "direct Coombs-positive" patient.

EXAMPLES

Example 1

Antigen Identification

The objective of this analysis is to identify, by means of specific monoclonal antibodies, antigens that are present at the surface of red blood cells from donors or from patients. Fluorescent beads are used to immobilize the anti-red blood cell antibodies. Antibodies of different antigenic specificities can thus be bound to various regions of beads that have different colours.

As for the red blood corpuscles, they are labelled with a fluorescent compound compatible with the wavelengths of the reporter laser of the apparatus sold under the name "Bioplex 200" by the company Bio-Rad.

After labelling, the red blood cells are incubated with the sensitized beads. It is thus possible to detect the red blood cells attached to the beads and thus to determine their antigenic specificities.

1.1—Material and reagents

Beads:

The beads used are manufactured by Luminex (Luminex Corp., Austin Tex., United States). They are superparamagnetic beads 8 μm in diameter, composed of polystyrene and methacrylic acid (COOH function).

In this example, fluorescent superparamagnetic beads having various bead regions 19, 21, 32, 34 (Internal Standard Beads (ISB)), 71 and 98 (Blank Beads (BB)) are used. The beads (ISB) having bead region 34 are functionalized with a rhodamine derivative and are used as an internal fluorescence control. These beads should produce fluorescence values of between 5000 and 15 000 RFI.

The region-98 BB beads are saturated with bovine albumin. These beads combined neither antigens nor antibodies and are therefore used to verify the absence of non-specific binding. These beads should produce fluorescence values of less than 1000 RFI.

Anti-human immunoglobulin monoclonal IgG antibody, clone 125A15 (Bio-Rad).
Anti-human IgM (mu) polyclonal antibody (Bio-Rad).
Anti-D IgG (clone H2D5D2F5), anti-Fya IgG (clone 5T72A13F5A93) and anti-S IgM (clone MS94) monoclonal antibodies (Bio-Rad, Millipore).
PKH26 cell labelling kit (Sigma).
Diluting medium sold under the names "ScanLiss" code 86442 and "Stabiliss" code 86550 by the company Bio-Rad.
Gel cards sold under the name "ScanGel Coombs" code 86432 for atypical antibody screening (Bio-Rad).
Gel cards sold under the names "ScanGelRhK" code 86428 and "ScanGel Neutral" code 86430 (Bio-Rad).
Phenotyped red blood cells sold under the names "ScanPanel" code 86593 and "ScanCell" code 86595 for atypical antibody screening by the gel card technique (Bio-Rad).
Concentrated phenotyped blood cell pellets conserved in SAG-MAN medium (EFS Nord de France).
Direct Coombs-positive and/or -negative red blood cells originating from patient samples.
Coating liquid or buffer (10 mM sodium phosphate, 150 mM NaCl, 0.1% (v/v) proclin.
Bovine serum albumin (BSA) (Millipore).
PBS buffer, pH 7.4 (7 mM sodium phosphate, 2.7 mM KCl, 136 mM NaCl).

1.2 Protocol
1.2.1. Sensitization of Beads with Blood Group Antibodies

Figure 1:
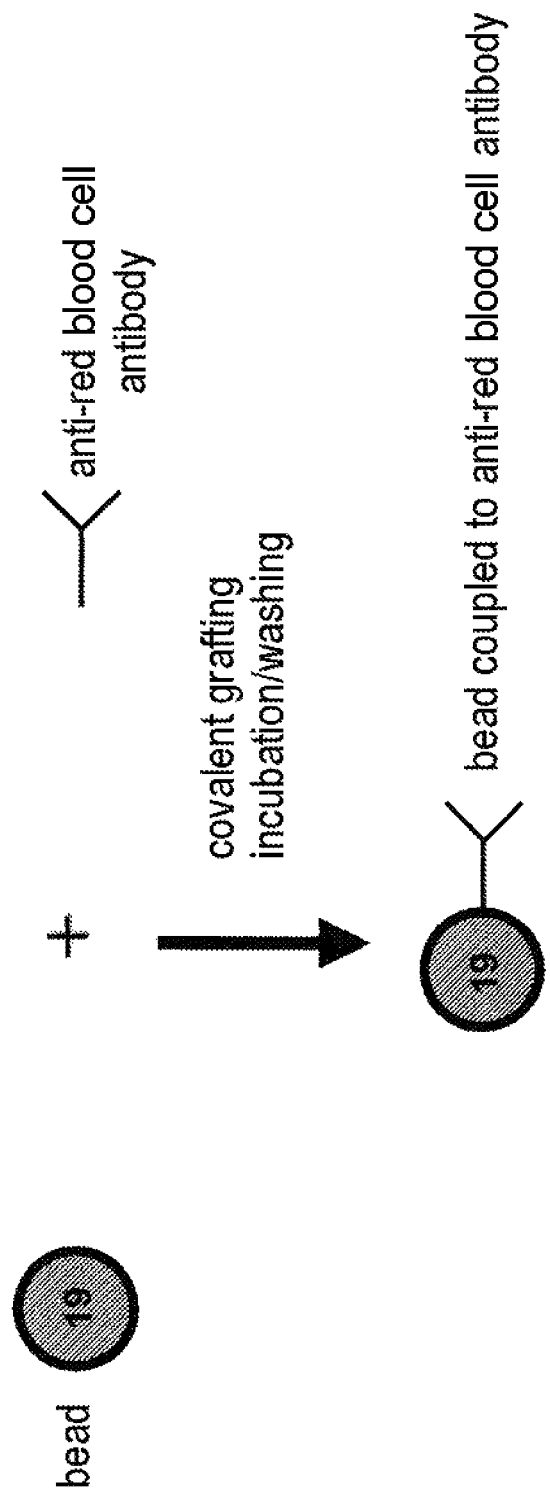
FIG. 1 is a scheme which illustrates a direct immobilization of antibodies on a Luminex® bead.
Figure 2:
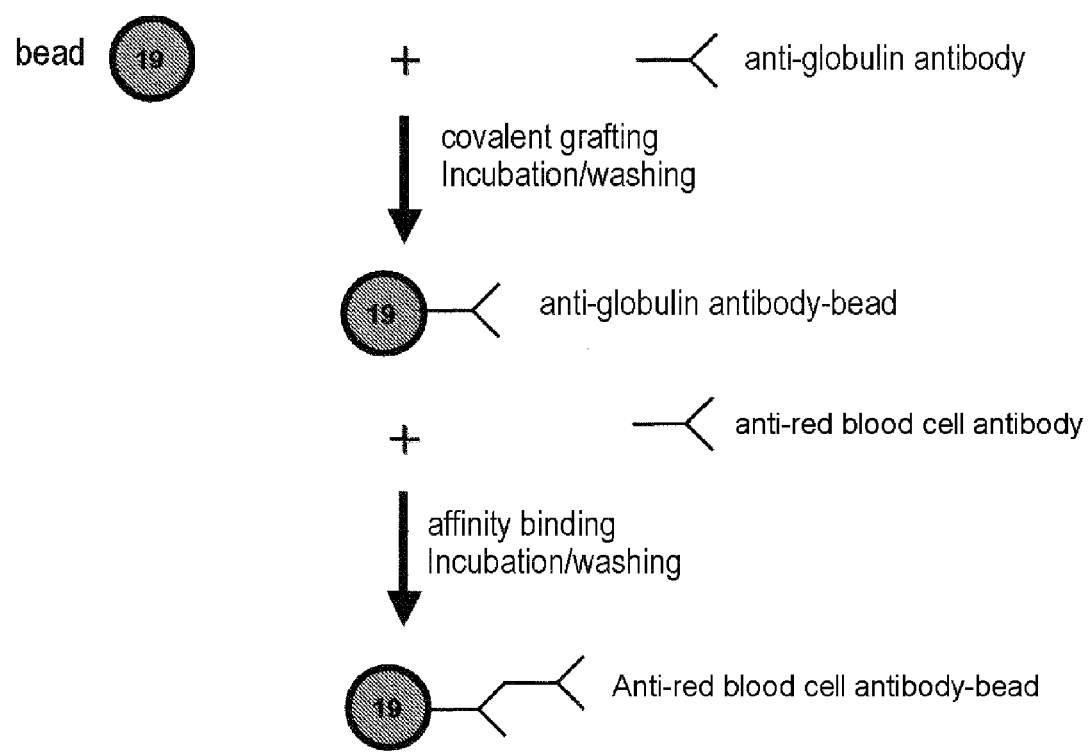
FIG. 2 is a scheme which illustrates an immobilization of antibodies on beads, by affinity, on a Luminex® bead.

The immobilization of the antibodies at the surface of the beads can be carried out according to two different principles. In the first case, the antibodies are immobilized by covalence directly on the beads (FIG. 1). The second approach consists in carrying out the immobilization of the anti-red blood cell antibodies noncovalently, by affinity. In this case, the attachment is carried out by means of an anti-immunoglobulin antibody attached by covalence to the bead in a first step (FIG. 2). This approach was selected in the examples presented.

Beads having bead regions 19, 21 and 32 were used for the covalent immobilization of the anti-human immunoglobulin. Fluorescent beads having bead region 71 were used for the covalent immobilization of the anti-human IgM. The carboxylic groups present at the surface of the beads were activated according to a technique involving a hydroxysuccinimide and a carbodiimide. The proteins could thus be immobilized via their amine groups.

The beads thus prepared are stored at +4° C. at a concentration of 3 mg/ml in PBS, pH 7.4, containing 10% (w/v) of BSA, 0.5% (v/v) of Tween 20 and 0.09% (w/v) of sodium azide.

The beads carrying the immobilized anti-human immunoglobulin can be sensitized with anti-D IgG or anti-Fya IgG blood group antibodies. The anti-immunoglobulin in fact allows the IgGs to bind via their Fc fragment. The blood group antibodies are therefore non-covalently immobilized on the beads using this principle. Each bead region is sensitized with an antibody of different specificity. The anti-immunoglobulin chosen has a high affinity for human immunoglobulins, thus allowing this binding to be stable over time.

The nonpurified anti-D and anti-Fya are used at the respective final concentrations of 30 and 10 µg/ml with beads functionalized with anti-Fc at 80 µg/mg.

The sensitization with the blood group antibodies is carried out in PBS, pH 7.4, with agitation at 37° C. for one hour.

After sensitization, the beads are rinsed several times and then stored at +4° C. in PBS, pH 7.4.

The beads carrying the immobilized anti-mu can be sensitized with the anti-S IgM. The anti-mu in fact allows binding of IgMs. The affinity of this anti-mu polyclonal serum is sufficient to ensure binding that is stable over time. The nonpurified anti-S is immobilized on beads functionalized with anti-mu at 40 µg/mg. The sensitization is carried out in PBS, pH 7.4, with agitation at 37° C. for one hour. After sensitization, the beads are rinsed several times and then stored at +4° C. in PBS, pH 7.4.

Before incubation with the red blood cells (test per se), the beads sensitized with the blood group antibodies are mixed with control region-34 beads (ISB) and control region-98 beads (BB).

1.2.2. Labelling of Red Blood Cells

Figure 3:
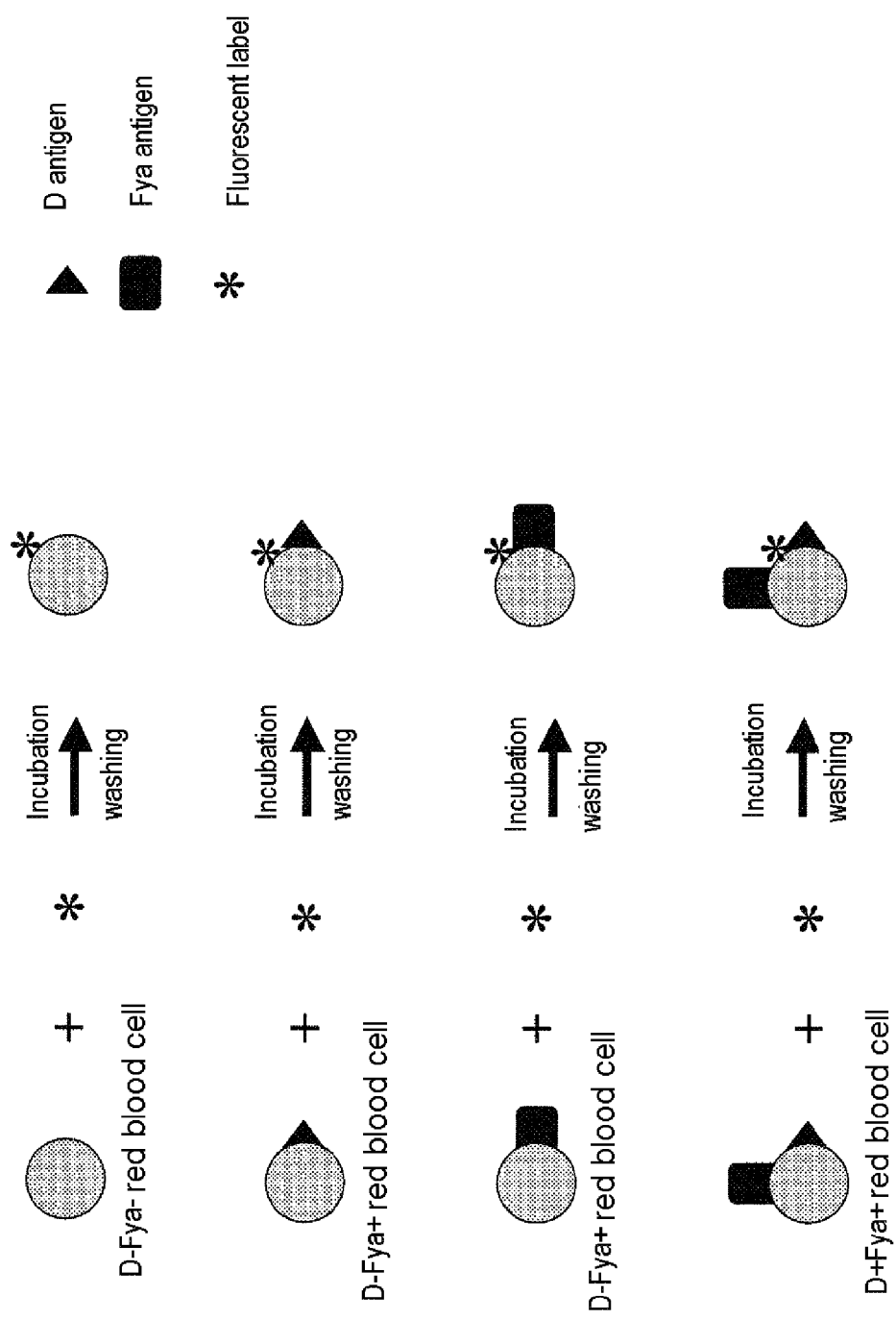
FIG. 3 is a scheme which illustrates the labelling of red blood cells of various phenotypes with a fluorescent intramembrane compound.
Figure 4:
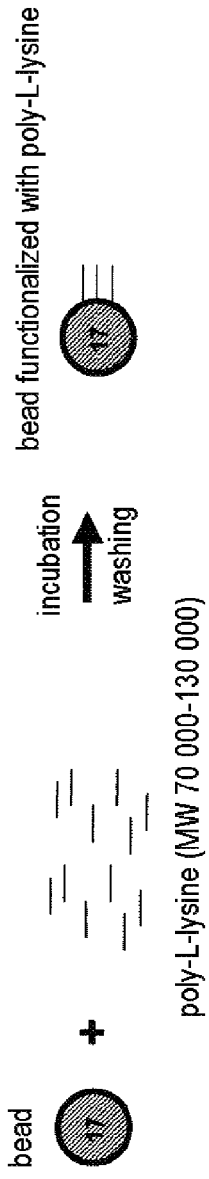
FIG. 4 is a scheme which illustrates a procedure for immobilizing red blood cells on Luminex® beads by means of poly-L-lysine.
Figure 4:

The labelling of red blood cells with a fluorescent compound can be carried out using various principles. In the examples presented, the red blood cells are labelled using PKH26, which is a fluorophore that is inserted into the red blood cell membrane. Red blood cells of varied phenotypes can thus be labelled according to an identical protocol (FIG. 3).

PKH26 is a fluorescent probe sold by the company Sigma. This probe has a maximum excitation at 551 nm and a maximum emission at 567 nm.

The kit includes the fluorescent label, which has a long aliphatic chain allowing it to be incorporated into the lipid layer of cell membranes, and also an isoosmotic aqueous diluent containing no salt, buffer or organic solvent. This diluent makes it possible to maintain the cell viability, the label solubility and the labelling efficiency at high levels. The labelling of red blood cells with PKH26 is carried out using the protocol recommended by the manufacturer. The red blood cells thus labelled are diluted in the Stabiliss buffer and stored in the dark at +4° C.

The quality, the viability and the stability of the labelled red blood cells are verified over time by carrying out phenotyping assays according to a gel technique. The antigenic integrity of the labelled red blood cells is compared with that of nonlabelled red blood cells. The quality and the stability of the fluorescent labelling are, for their part, studied by carrying out fluorescence measurements using the "Bioplex 200" apparatus from Bio-Rad.

1.2.3. Incubation of Antibody-Beads and Red Blood Cells

In order to demonstrate the feasibility and verify the specificity of the grouping according to the technology in accordance with the invention, the inventors carried out the reactions in a unitary manner. In this case, the beads functionalized with the antibodies of interest are incubated individually with red blood cells of varied phenotypes.

In the case of the multiplexed reactions, different blood samples are brought into contact individually with beads having different bead regions and sensitized with antibodies of different specificities. This type of experiment made it possible to verify the possibility of detecting several antigenic specificities in the same test sample.

The sensitized beads are mixed with the red blood cells so as to obtain a red blood cell/bead ratio of approximately 50 to 150. The mixture is incubated for 15 minutes with agitation at 37° C.

After incubation, the bead-red blood cell complexes are washed several times with distilled water.

1.2.4. Measurements by Flow Cytometry Using the "Bioplex 200" Automated Device From the Company Bio-Rad After the final wash and before the measurements, the complexes are diluted with 185 µl of "coating liquid" medium. For each test, 25 µl of suspension are automatically injected into the apparatus. The measurements are carried out by capture of 250 beads per region.

For each grouping/phenotyping series, systematic controls are carried out in order to verify the specificity of the reactions studied.

1.3. Simplex/Multiplex Phenotyping/Grouping Examples

The objective of this series of tests is to demonstrate the feasibility of the phenotyping/grouping of red blood cells in unitary and/or multiplexed mode. The D, Fya and S antigens are selected as models. Beads sensitized with an anti-human immunoglobulin or anti-mu chain antibody are used to immobilize anti-D, anti-Fya and anti-S antibodies.

1.3.1. Unitary Phenotyping of RH D-Positive Red Blood Cells

The beads sensitized with the anti-D antibody were incubated with Rh D-positive and Rh D-negative red blood cells labelled with PKH26, using a red blood cell number/bead number ratio of 150.

Two RH D-positive red blood cells and two RH D-negative red blood cells were used. Each sample was injected into the apparatus in duplicate.

The RH D-positive red blood cells produce strongly positive signals of the order of 21 000 to 25 000 RFI, whereas the RH D-negative red blood cells exhibit negative signals of between 40 and 400 RFI.

The ISB 34 control beads that give signals of the order of 6500 RFI and the BB 98 control beads that give less than 1000 RFI validate the results. The various negative controls carried out exhibit signals of between 15 and 400 RFI, confirming the specificity of the reactions. The RH D-positive and RH D-negative red blood cells do not in fact bind to the beads in the absence of anti-D antibodies.

These results demonstrate the possibility of distinguishing very clearly the RH D-positive and RH D-negative red blood cells and therefore of identifying the D antigen at the surface of red blood cells.

The unitary phenotyping of Fya and S red blood cells can be carried out according to the same principle, using isotype G-specific or isotype M-specific antibodies.

1.3.2. Multiplex Phenotyping of D, Fya and S Red Blood Cells

The principle of the multiplexed phenotyping is summarized in FIGS. 5A to 5D.

In this case, region-19 beads sensitized with an anti-D antibody were mixed with region-21 beads sensitized with an anti-Fya antibody and also with region-71 beads sensitized with an anti-S antibody.

This mixture of beads was incubated with red blood cells having different D, Fya and S phenotypes: D+Fya+S+/D+Fya−S−/D−Fya+S−/D−Fya−S−/D−Fya+S+/D−Fya+S+/D+Fya+S−. A red blood cell number/bead number ratio of 50 was used. Positive signals of between 13 000 and 29 000 RFI are obtained when the beads sensitized with a given antibody bind a red blood cell having the corresponding antigenic specificity.

A perfect correlation is observed between the fluorescent signals measured and the phenotype of the red blood cells used to carry out the test.

When a bead sensitized with an antibody is brought into contact with a red blood cell that does not carry the corresponding antigen, a signal of less than 1000 RFI is obtained.

Moreover, the controls carried out with beads not antibody-sensitized produce negative signals irrespective of the red blood cell used.

These results demonstrate that the signals measured are specific: the bead-red blood cell binding occurs only when an antigen-antibody pair is involved.

The results obtained with the control beads ISB 34 (11 000 RFI) and BB 98 (less than 1000 RFI) validate the analyses.

The intra-test variation coefficients are between 1% and 10%, which demonstrates a satisfactory intra-test reproducibility.

These results demonstrate the feasibility of the three-parameter multiplexed phenotyping of red blood cells according to the technology according to the invention.

1.3.3. Multiplexed Phenotyping of Direct Coombs-Positive (CD+) Red Blood Cells

The use of the multiplexed approach with microbeads makes it possible to identify the CD+ nature and to phenotype the red blood cells simultaneously according to a principle described in FIG. 6.

Region-32 beads sensitized with the anti-Fc antibody are mixed with region-19, -21 and -71 beads respectively sensitized with an anti-D, anti-Fya and anti-S antibody. The CD+ red blood cells, sensitized in vivo with an antibody, can bind to the anti-human immunoglobulin carried by the region-32 beads, thereby making it possible to identify the CD+ characteristic. Moreover, these red blood cells can also bind to the region-19, -21 and -71 beads carrying the antibodies specific for the D, Fya and S antigens, according to the specificities present on the red blood cell membrane.

This approach was demonstrated using a red blood cell number/bead number ratio of the order of 40.

The ISB 34 and BB 98 control beads produce expected signals, i.e. respectively of the order of 13 000 RFI and less than 1000 RFI, and validate the results.

The two CD+ red blood cells produce positive signals greater than 30 000 RFI with the region-32 beads sensitized with the anti-human immunoglobulin antibody. The two CD− negative red blood cells produce, for their part, negative signals of less than 500 RFI with this same bead region. These results demonstrate the possibility of identifying CD+ red blood cells by virtue of their specific binding using an anti-globulin coupled beforehand to a bead of given bead region.

Furthermore, the results also demonstrate that the multiplexed phenotyping of the erythrocyte antigens of CD+ red blood cells can be carried out simultaneously with the identification of the CD+ nature. In fact, one of the CD+ red blood cells is phenotyped D+Fya−S− and the other D+Fya+S+.

The S phenotype of these two samples was verified according to a conventional technique using anti-S antibodies of IgM type. The results obtained are perfectly correlated with those obtained according to the new technique.

On the other hand, as regards the anti-Fya phenotype, this same analysis could not be carried out. There is in fact no reagent of IgM type for phenotyping red blood cells.

However, a difference is observed for the Fya phenotype according to the CD+ red blood cell analyzed, which validates the results and makes it possible to exclude a phenomenon of nonspecific binding.

The variation coefficients are for most of the samples between 1% and 5%, which shows a satisfactory intra-test reproducibility.

Example 2

Detection of Phosphatidylserine, a Marker of Erythrocyte Ageing

The demonstration of markers of erythrocyte ageing is of value in studying red blood cell populations in blood transfusion (Cardo L J et al Transfus Apher Sci, 2008 April; 38(2): 141-7) but also in studying the phenomena involved in certain blood pathologies such as thalassaemia (Basu S et al Br J Haematol, 2008 April; 141(1): 92-9). Erythrocyte ageing is reflected in particular by the appearance of a structure called phosphatidylserine (PS) at the surface of the erythrocytes.

The test of the invention can be readily implemented for detecting this molecule at the surface of red blood cells.

For this, fluorescent beads are used to immobilize the red blood cells to be tested, via poly-L-lysine (PLL).

These beads are then brought into contact with an anti-phosphatidylserine antibody in an incubation phase.

After a washing step, the binding of the anti-phosphatidylserine to the red blood cell is detected by incubation of the bead-red blood cell complexes with an anti-Fc (IgG) secondary antibody labelled with phycoerythrin (PE).

A final washing step intended to eliminate the unbound anti-Fc(IgG)-PE is carried out. The bead-red blood cell complexes are then read using the BioPlex200 apparatus.

Red blood cells of different ages, obtained from blood bags, are used as a standard range.

The invention claimed is:

1. An in vitro method for identifying a plurality of antibodies in a biological sample against antigenic molecules carried by erythrocytes, said antigenic molecules comprising phosphatidylserine, human leukocyte antigen (HLA) antigens, chemical products or medicaments or degradation products thereof, by
bringing said biological sample into contact, in a single test receptacle, or in several separate test receptacles, with groups of distinguishable beads, each group of distinguishable beads carrying (1) erythrocytes carrying said antigenic molecules or (2) erythrocyte membrane fragments carrying said antigenic molecules the antigenic molecules carried by (1) erythrocytes or (2) erythrocyte membrane fragments differing between each group of distinguishable beads, under conditions which allow the antibodies or activated serum complement fractions present in the sample to bind to said antigenic molecules on the erythrocytes or the erythrocyte membrane fragments without agglutination,
eliminating the antibodies or activated serum complement fractions which have not bound to antigenic molecules carried by said erythrocytes or said erythrocyte membrane fragments, labelling antibodies bound to said antigenic molecules and/or the bound activated serum complement fractions, and
analyzing the mixture so as to identify the group of beads having bound the labelled antibodies or the labelled activated serum complement fractions, thereby allowing the identification of the antibodies present in said biological sample that specifically bind to said antigenic molecules carried by said erythrocytes or said erythrocyte membrane fragments.

2. The method according to claim 1, wherein the method comprises haemolysis of said erythrocytes prior to said analysis of the mixture, said haemolysis resulting in degradation of haemoglobin within said erythrocytes.

3. The method according to claim 1, wherein the distinguishable beads are superparamagnetic or magnetic or magnetizable beads.

4. The method according to claim 1, wherein the distinguishable beads emit luminescent or fluorescent signals.

5. The method according to claim 1, wherein the erythrocytes are labelled with a fluorescent compound.

6. The method according to claim 1, wherein the antibodies are labelled by bringing into contact with an anti-human globulin antibody carrying a fluorescent, luminescent or radioactive label.

7. The method according to claim 1, wherein the biological sample is selected from the group consisting of whole blood, plasma, serum and a blood cell pellet.

8. The method according to claim 1, further comprising the quantification of the identified antibodies.

9. The method according to claim 1, wherein the antigenic molecule is phosphatidylserine.

10. The method according to claim 1, wherein the analysis of the mixture is carried out by flow cytometry.

11. The method of claim 1, wherein the beads carry erythrocytes.

12. The method of claim 1, wherein the beads carry erythrocyte membrane fragments.

13. A set of reagents comprising a group of distinguishable beads, said group of distinguishable beads being detectably distinguishable according to a physicochemical property selected from the group consisting of size, density, roughness, absorbance, fluorescence, luminescence, paramagnetism, magnetism and ability to be magnetized and carrying (1) erythrocytes carrying antigenic molecules or (2) an erythrocyte membrane fragment carrying antigenic molecules, said antigenic molecules comprising phosphatidylserine, human leukocyte antigen (HLA) antigens, chemical products or medicaments or degradation products thereof.

14. An in vitro method for identifying a plurality of antigenic molecules carried by the erythrocytes of an individual, and/or for identifying a plurality of antibodies against antigenic molecules carried by erythrocytes, in a biological sample, said antigenic molecules comprising phosphatidylserine, human leukocyte antigen (HLA) antigens, chemical products or medicaments or degradation products thereof, said method comprising:
a) identifying a plurality of antigenic molecules carried by the erythrocytes of an individual, by
(i) bringing said sample containing erythrocytes into contact, in a single test receptacle, or in several separate test receptacles, with groups of distinguishable beads, each group of distinguishable beads carrying a given antibody, specific for an antigenic molecule carried by erythrocytes, which differs from one group of beads to the other, under conditions which allow the erythrocytes to bind to the antibodies, without agglutination, said erythrocytes being labelled before or after they have been brought into contact with said groups of beads,
(ii) eliminating the erythrocytes which have not bound to said antibodies, and
(iii) analyzing the mixture so as to identify the group of beads having bound the labelled erythrocytes, thereby allowing the identification of the antigens carried by the erythrocytes detected; and
b) identifying a plurality of antibodies in a biological sample against antigenic molecules carried by erythrocytes, said antigenic molecules comprising phosphatidylserine, human leukocyte antigen (HLA) antigens, chemical products or medicaments or degradation products thereof, by (i) bringing said sample into contact, in a single test receptacle, or in several separate test receptacles, with groups of distinguishable beads, each group of distinguishable beads carrying (1) erythrocytes carrying said antigenic molecules or (2) erythrocyte membrane fragments carrying said antigenic molecules, the antigenic molecules carried by (1) erythrocytes or (2) erythrocyte membrane fragments differing between each group of distinguishable beads, under conditions which allow the antibodies or activated serum complement fractions present in the sample to bind to said antigenic molecules on the erythrocytes or to the erythrocyte membrane fragments without agglutination, (ii) eliminating the antibodies or activated serum complement fractions which have not bound to antigenic molecules carried by said erythrocytes or said erythrocyte membrane fragments, (iii) labelling antibodies bound to said antigenic molecules and/or the bound activated serum complement fractions, and (iv) analyzing the mixture so as to identify the group of beads having bound the labelled antibodies or the labelled activated serum complement fractions, thereby allowing the identification of the antibodies present in said biological sample that specifically bind to said antigenic molecules carried by said erythrocytes or said erythrocyte membrane fragments.

15. The method according to claim 14, in which the identifying of the antigens according to a) and the identifying of the antibodies according to b) are carried out simultaneously and in the same receptacle.

16. The method according to claim 14, wherein the analysis of the mixture is carried out by flow cytometry.

17. The method according to claim 14, wherein the method comprises haemolysis of said erythrocytes prior to said analysis of the mixture, said haemolysis resulting in degradation of haemoglobin within said erythrocytes.

18. The method according to claim 14, wherein the distinguishable beads are superparamagnetic or magnetic or magnetizable beads.

19. The method according to claim 14, wherein the distinguishable beads emit luminescent or fluorescent signals.

20. The method according to claim 14, wherein the erythrocytes are labelled with a fluorescent compound.

21. The method according to claim 14, wherein the antibodies are labelled by bringing into contact with an anti-human globulin antibody carrying a fluorescent, luminescent or radioactive label.

22. The method according to claim 14, wherein the biological sample is selected from the group consisting of whole blood, plasma, serum and a blood cell pellet.

23. The method according to claim 14, further comprising the quantification of the identified antibodies.

24. The method according to claim 14, wherein the antigenic molecule is phosphatidylserine.

25. The method of claim 14, wherein the beads carry erythrocytes.

26. The method of claim 14, wherein the beads carry erythrocyte membrane fragments.

27. A set of reagents comprising groups of distinguishable beads, each group being detectably distinguishable according to a physicochemical property selected from the group consisting of size, density, roughness, absorbance, fluorescence, luminescence, paramagnetism, magnetism or and ability to be magnetized and belonging to at least two different groups, one of the groups carrying a capture antibody specific for an antigenic molecule carried by erythrocytes, and the other group carrying (1) erythrocytes carrying antigenic molecules or (2) an erythrocyte membrane fragment carrying antigenic molecules, said antigenic molecules comprising phosphatidylserine, human leukocyte antigen (HLA) antigens, chemical products or medicaments or degradation products thereof.

* * * * *